(12) United States Patent
Luloh et al.

(10) Patent No.: US 6,743,168 B2
(45) Date of Patent: Jun. 1, 2004

(54) ENDOSCOPE SYSTEM AND METHOD OF USE

(75) Inventors: K. Peter Luloh, Longwood, FL (US); Michael Annen, Sanford, FL (US)

(73) Assignee: Insight Instruments, Inc., Stuart, FL (US)

(*) Notice: Subject to any disclaimer, the term of this patent is extended or adjusted under 35 U.S.C. 154(b) by 162 days.

(21) Appl. No.: 10/066,328

(22) Filed: Feb. 1, 2002

(65) Prior Publication Data

US 2002/0161279 A1 Oct. 31, 2002

Related U.S. Application Data

(60) Provisional application No. 60/266,354, filed on Feb. 2, 2001.

(51) Int. Cl.[7] ................................................. A61B 1/06
(52) U.S. Cl. ........................................ 600/167; 600/112
(58) Field of Search ................................ 600/112, 118, 600/131, 163, 167, 173; 359/694, 823

(56) References Cited

U.S. PATENT DOCUMENTS

| | | | |
|---|---|---|---|
| 3,801,181 A | | 4/1974 | Kitano et al. |
| 3,936,149 A | | 2/1976 | Imai |
| 4,515,444 A | | 5/1985 | Prescott et al. |
| 4,641,927 A | | 2/1987 | Prescott et al. |
| 4,735,491 A | | 4/1988 | Takahashi |
| 4,895,433 A | | 1/1990 | Takahashi et al. |
| 4,911,148 A | * | 3/1990 | Sosnowski et al. ......... 600/136 |
| 4,969,450 A | * | 11/1990 | Chinnock et al. .......... 600/109 |
| 5,085,221 A | | 2/1992 | Ingebrigtsen et al. |
| 5,093,719 A | | 3/1992 | Prescott |
| 5,095,887 A | | 3/1992 | Leon et al. |
| 5,411,500 A | * | 5/1995 | Lafferty et al. ................ 606/2 |
| 5,876,327 A | * | 3/1999 | Tsuyuki et al. ............. 600/112 |
| 6,036,637 A | * | 3/2000 | Kudo .......................... 600/173 |
| 6,066,090 A | | 5/2000 | Yoon |
| 6,117,071 A | * | 9/2000 | Ito et al. ..................... 600/168 |
| 6,292,221 B1 | * | 9/2001 | Lichtman .................... 348/345 |
| 6,464,631 B1 | * | 10/2002 | Girke et al. ................. 600/109 |
| 6,471,653 B1 | | 10/2002 | Jordfald et al. |
| 6,473,116 B1 | | 10/2002 | Takahashi |
| 6,478,730 B1 | * | 11/2002 | Bala et al. ................... 600/121 |

OTHER PUBLICATIONS

William G. French, A. David Pearson, refractive Index Changes Produced In Glass by Ion Exchange, American Ceramic Society, Columbus, Ohio, Bulletin, vol. 49, No. 11 (1970), pps. 974–977.

\* cited by examiner

*Primary Examiner*—Roy D. Gibson
(74) *Attorney, Agent, or Firm*—James H. Beusse; Beusse Brownlee Wolter Mora & Maire, P.A.

(57) ABSTRACT

An endoscope for eye surgery incorporates a handle having a camera and an electric motor driven lens assembly for enabling a user to focus the camera during surgery without manually adjusting the focus. The endoscope includes a probe attached by a rotatable bayonet type connector with a simple pivoting lever to release the probe from the handle. The motor drive system incorporates spring biasing to compensate for overruns of a drive nut on a lead screw when the user attempts to exceed the focal range of the lens assembly.

23 Claims, 5 Drawing Sheets

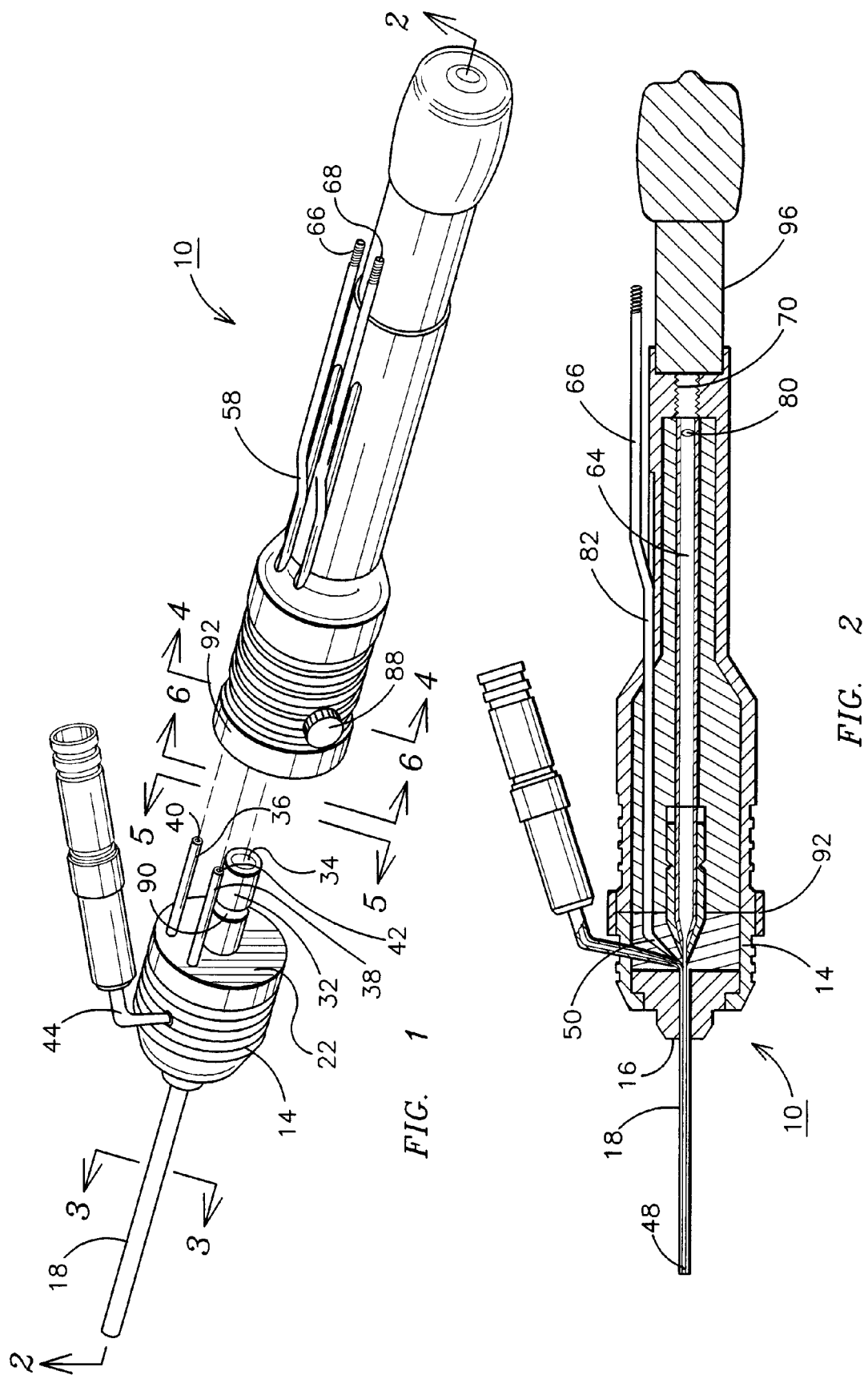

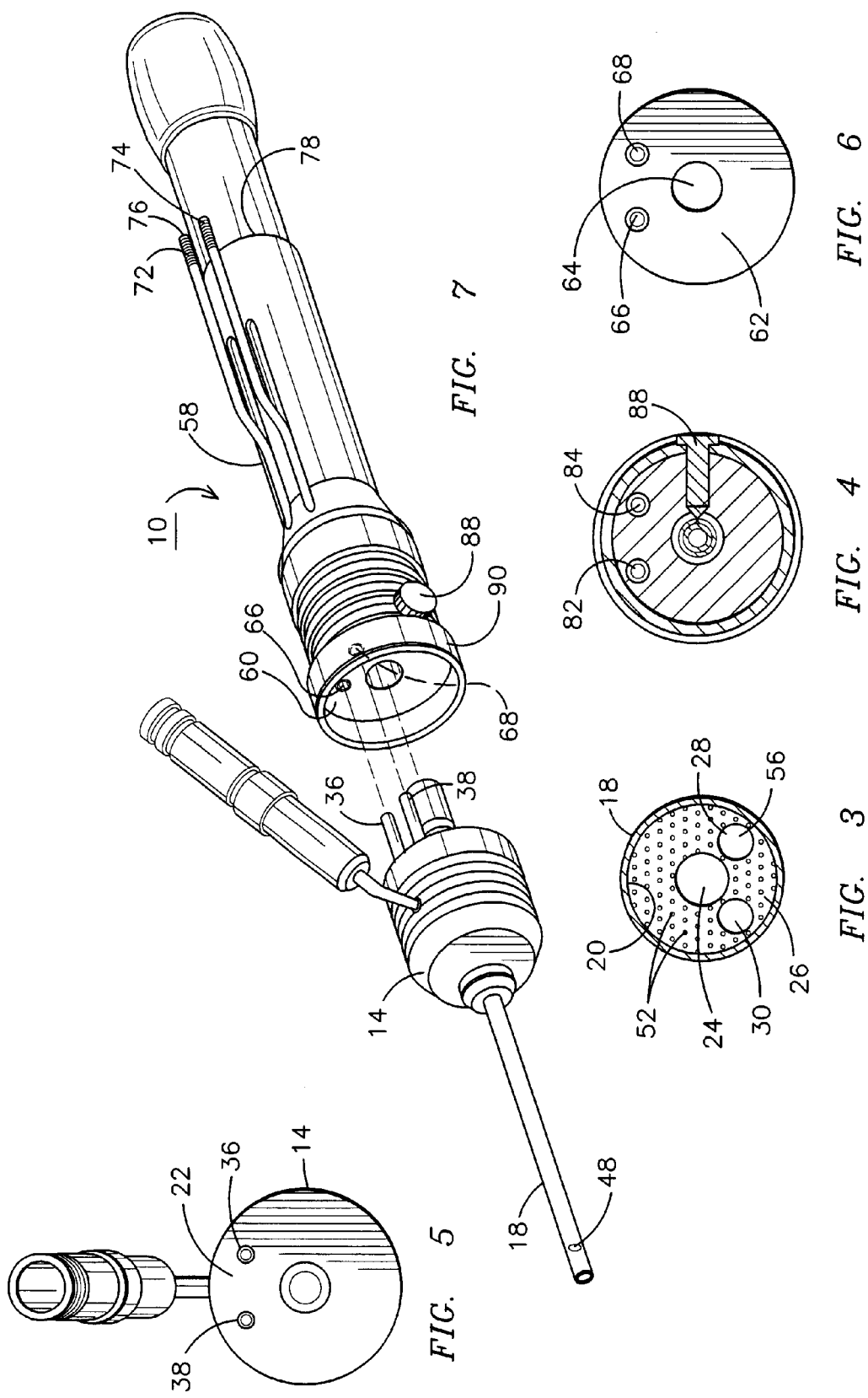

ENDOSCOPE SYSTEM AND METHOD OF USE

This application claims the benefit of U.S. Patent Application Serial No. 60/266,354, filed on Feb. 2, 2001 which is specifically incorporated herein by reference.

BACKGROUND OF THE INVENTION

The present invention relates to an endoscopic system and method of use and, more particularly, an endoscopic system and method useful in eye surgery for illuminating, viewing, lasing and washing an area of an eye of a patient to be operated upon.

DESCRIPTION OF THE BACKGROUND ART

The use of endoscopes and other surgical devices of known designs and configurations is known in the prior art.

By way of example, the prior art includes U.S. Pat. No. 5,093,719 to Prescott entitled Endoscopic Gradient Index Optical Systems. This patent discloses gradient index endoscopic or borescopic systems in forms ranging from basic to more complex depending on the optical task. The basic form comprises a gradient index objective of less than a quarter period in length followed by a gradient index relay whose length is at least one-quarter period longer than the distance of the first image of the object into the relay. The numerical aperture of the objective is preferably larger than that of the relay to provide a wide angle endoscope with an entrance aperture tunnel preceding the objective. In one embodiment with a line-of-view prism, the entrance tunnel is placed in the most restricted aperture within the prism thus minimizing or eliminating vignetting of the field of view. A second embodiment of this subsystem is an endomicroscope wherein the entrance pupil moves and changes size as the ocular focus of the system is changed. The endoscope retains the maximum possible Lagrangian of the system as limited by the numerical aperture and diameter of the relay for all foci. The prior art also includes U.S. Pat. No. 5,095,887 to Leon entitled Microscope-Endoscope Assembly Especially Usable in Surgery. This patent relates to an optical assembly comprising a microscope including a binocular with a pair of oculars, an optical body and an objective lens and an optical path; and an endoscope provided with an extension, an outlet ocular, and an optical path. A commutating modulus is disposed between the binocular and the optical body of the microscope and the outlet ocular of the endoscope so as to enable an observer whose eyes are located at each ocular of the microscope to observe selectively either (a) the optical path of the microscope or (b) the optical, or electronic, path of the endoscope or (c) both optical paths simultaneously to scan an object to be investigated.

In this respect, the endoscope system of the present invention departs substantially from the conventional concepts and designs of the prior art, and in so doing provides a method and apparatus with selectively uncouplable and couplable components primarily developed for the purpose of illuminating and/or viewing and/or lasing and/or washing an area of a patient, such as en eye, to be operated upon.

SUMMARY OF THE INVENTION

The present invention comprises a new and improved endoscope system and method of use for illuminating, viewing, lasing, and washing an eye area of a patient being operated upon comprising, in combination a distally positioned needle component in a generally cylindrical configuration. The needle portion has a distal face and a centrally located tubular needle with a major bore extending distally therefrom and a generally planar proximal face. The major bore has four minor bores axially aligned within the major bore. The proximal face has a plurality of proximally extending tubes including an enlarged viewing tube with an observation bore axially aligned with the major bore of the needle and with two supplemental tubes extending proximally from the proximal face. Each supplemental tube has a bore and an additional tube extending laterally from the needle component. The additional tube is couplable proximal to a source of washing fluid. The first minor bore is in axial alignment with the observation bore with a first lens within the first minor bore and observation bore with the first lens adapted to transmit optical images from the distal end of the needle to the proximal end of the observation tube. The second minor bore and a supplemental tube are coupled through a first angled transistion bore and contain first optical strands for effecting illumination at the distal end of the needle. The third minor bore and the other supplemental tube are coupled through a second angled transistion bore and contain a second optical strand for lasing or fluid infusing. A proximally positioned handle component has a proximal end and an essentially flat distal end with a plurality of axially aligned bores therethrough. It includes a central bore in axial alignment with the observation bore of the needle portion for the receipt of the main tube terminating at the proximal end with internal threaded recess for the removable receipt of a viewing instrument. A second lens is located within the central bore in optical communication with the first lens of the needle component and illumination fibers within one of the supplemental bores in optical alignment with the illumination fibers of the needle component. A lasing fiber or infusion tube is located in the other of the supplemental bores in optical alignment with the lasing fiber of the needle component. The bores at the distal end of the handle component are sized for the receipt of the observation tube and supplemental tubes of the needle component. A bayonet type connector enables rapid separation of the needle component to the handle component. A pivotable locking level prevents separation of the components during use. The handle includes an electric motor-driven focusing assembly to enable the user to rapidly change focus while using the device. Also included is the method of using an endoscope system which includes the step of providing the components as described above including the further step of uncoupling and coupling the needle and handle components as may be required for a particular application.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved endoscope system and method which has all the advantages of the prior art surgical devices of known designs and configurations but with added capabilities.

It is another object of the present invention to selectively uncouple and couple components of an endoscope system to meet the requirements of a particular application.

It is a further object of the present invention to provide a new and improved endoscope system which is of a durable and reliable construction.

Still yet another object of the present invention is to tailor miniaturized surgical systems for illuminating and/or viewing and/or lasing and/or cleaning as needed for a required observation or treatment.

Still another object of the present invention is to illuminate, view, lase and wash an area of a patient to be operated upon.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated the preferred embodiment of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an exploded perspective illustration of the preferred embodiment of the endoscope system constructed in accordance with the principles of the present invention;

FIG. 2 is a cross-sectional view of the device shown in FIG. 1 taken axially along the length thereof along line 2—2 with the needle component and handle component being coupled for operation and use;

FIGS. 3 and 4 are cross sectional views taken along lines 3—3 and 4—4 respectively of FIG. 1, FIG. 3 being greatly enlarged;

FIGS. 5 and 6 are end elevational views taken along lines 5—5 and 6—6 respectively of FIG. 1;

FIG. 7 is an exploded perspective view similar to FIG. 1 but taken from the opposite side thereof;

Similar reference characters refer to similar parts throughout the several views of the drawings.

DESCRIPTION OF THE PREFERRED EMBODIMENT

Figure 8:
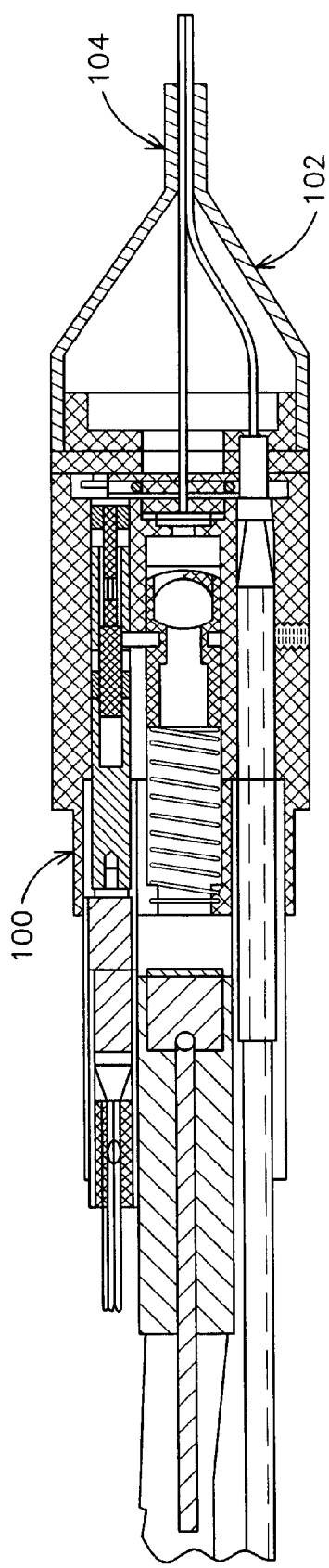
FIG. 8 is a cross-sectional view of an endoscope in accordance with one embodiment of the present invention.
Figure 10:
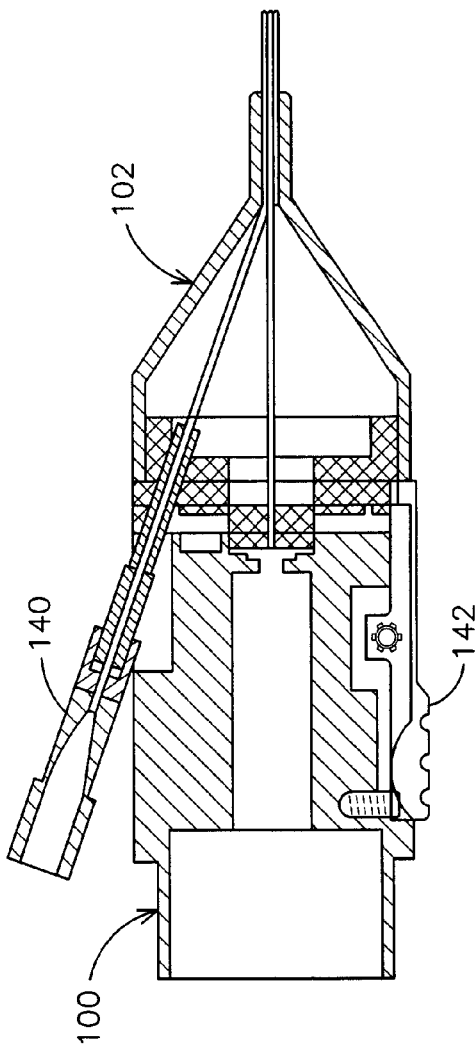
FIG. 10 is an enlarged view of the probe end of the endoscope of FIG. 8.

With reference now to the drawings, and in particular to FIGS. 1 through 7, thereof, an example of one existing form of endoscope system is shown. The endoscope 10 includes a distally positioned needle component 14 as one of its two primary components. See FIGS. 1, 2 and 7. At least a portion of the needle component is preferably formed in a generally cylindrical configuration. The needle component has a distal face 16 and a centrally located tubular needle 18 extending distally from the center of the distal face. The needle has a major bore 20 extending axially and centrally located within the entire length of the needle. The needle component is formed with a generally planar proximal face 22. As can best be seen with reference to FIG. 3, the major bore of the needle has four minor bores 24, 26, 28, 30 axially oriented within the major bore for purposes as will be later described. The proximal face 22 of the needle component has a plurality of proximally extending tubes. Such tubes include an enlarged viewing tube 32 with an observation bore 34 axially aligned with, and an extension of, the centrally oriented first minor bore 24 of the needle. The proximally extending tubes also include, in the preferred embodiment, two supplemental tubes 36, 38 extending proximally from the proximal face. Each supplemental tube has a bore 40, 42. Further, an additional tube 42 extends laterally and proximally from the needle component. The additional tube is couplable proximally to a source of washing fluid, not shown.

The first minor bore 24 of the needle is in axial alignment with the observation bore 34 of the viewing tube. A first lens 48 is located within the first minor bore and the observation bore 34. The first lens 48 is the first optical component and is adapted to transmit optical images from the distal end of the needle to the proximal end of the viewing tube.

As can be best seen in FIG. 2, the second minor bore 26 and the first supplemental tube 36 are optically coupled through a first angled transition bore 50 and contain a second optical element, strands 52 for effecting illumination of the area to be viewed adjacent to the distal end of the needle. The optical strands are located within the major bore of the needle in regions other the locations of the other optical elements. Such regions are considered the second minor bore. The third minor bore 28 and the second supplemental tube 38 are coupled through a second angled transistor bore 54. Note again FIG. 2. Such bores and tube contain a third optical element, an optical strand 56. Such optical strand functions for lasing at the area being viewed.

The fourth minor bore 30 is directly coupled to a source of pressurized fluid through the additional tube 44. Such bore and tube are in operative communication, one with the other, and are normally empty except when a fluid from the pressurized source, not shown, is employed to inject a washing or irrigation fluid against the area of the patient being viewed and/or operated upon.

A proximally positioned handle component 58 constitutes the second major component of the endoscope system. Such handle component has an essentially flat distal end 60. It also has a proximal end 62. The proximal end includes a plurality of axially parallel bores 64, 66, 68 therethrough. Such bores include an enlarged central bore 64 in axial alignment with the viewing tube 52 of the needle portion for the receipt of the viewing tube. Bores 66 and 68 at their distal ends are sized and positioned for the receipt of the supplemental tubes 36, 38 of the needle component. Compare FIGS. 1, 6 and 7. The handle component terminates at its proximal end with a centrally located, internal threaded recess 70 for the removable receipt of a viewing instrument, not shown. Additionally, two supplemental tubes 72, 74 extend through the handle component from the distal end to and beyond the proximal end. Such tubes terminate proximally with threaded ends 76, 78.

A second lens 80 is located within the central bore adjacent to the proximal end of the handle component in optical communication with the first lens 48 located adjacent to the distal end of the needle component. Such lenses function together to transmit images from the distal end of the needle to the proximal end of the handle component and rearwardly thereof to the viewing instrument. In addition, illumination strands 82 are located within the first supplemental tube 72 in operative alignment with the strands 52 of the second minor bore of the needle. A lasing strand 84 is located in the second of the supplemental tube 74 in axial alignment with the lasing strand 56 of the third minor bore of the needle.

The threaded ends 76, 78 of the supplemental tubes 72, 74 are adapted to be coupled to a source of illumination and to a laser source, respectively, when the needle component and handle component are coupled together for operation and use. Neither the source of illumination nor the laser source nor the above-referred to source of pressurized fluid are shown since such are essentially conventional in their constructions. Typical conventional constructions are described and referred to in the aforementioned U.S. Pat. No. 5,03,719 to Prescott.

The bores 64, 66, 68 at the distal end of the handle component are sized for the separable receipt of the viewing tube 52 and supplemental tubes 30, 32 of the needle component. This arrangement allows for the use of various needle components having various optical elements with various handle components having corresponding optical elements. For example, one needle component may be used with a variety of handle components. Conversely, one handle component may be used with a variety of needle components. In addition, the separability of the needle and handle components allows for different first and second lenses to be utilized one with another for tailoring a lens system for a particular application.

A threaded radial bore 86 is located in the handle component. An associated set screw 88 is threadedly received within the radial bore. The radially end of the set screw is located to be positioned within an annular recess 90 formed in the exterior surface of the viewing tube during operation and use of the system. These features are best seen in FIGS. 2 and 4. This allows for the selective separation of the major components as well as for the secure coupling between the needle component and the handle component as may be needed for a particular application.

A collar 92 is also located at the distal end of the handle component. The collar extends distally from the distal end of the handle component, circumferentially around the entire handle component for 360 degrees. The collar functions to receive and properly position the proximal end of the needle component to the distal end of the handle component during operation and use of the system. A collar extending around less than 360 degrees has also been found to function properly.

While the endoscope shown in FIGS. 1–7 is a substantial improvement over other endoscopes, it has been found that additional improvements are needed to simplify exchanging probes to handles during operations on patients when the fragile GRIN lens is often broken and also to enable better focusing of the viewing camera during such operations. FIGS. 8–11 illustrate such an improved endoscope.

Figure 9:
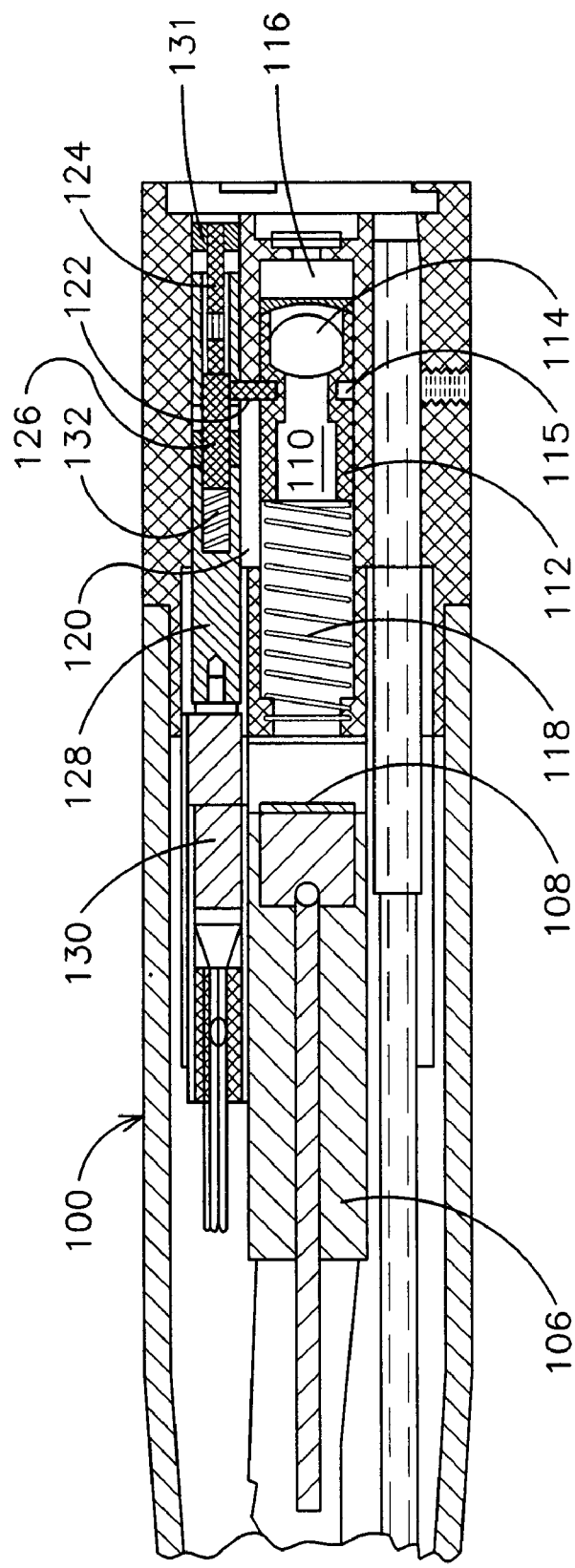
FIG. 9 is an enlarged view of the handle assembly of FIG. 8.

The present invention is an improved form of the endoscope described above. Turning now to FIG. 8, is shown a cross-sectional view of an endoscope incorporating the teachings of the present invention. The endoscope comprises a handle portion 100 and a detachable probe portion 102. A needle 104 containing the optical and other components described above with regard to FIGS. 1–7 extends from the end of the endoscope. FIG. 9 is an enlarged view of the handle portion 100. Within the handle portion 100 there is a camera 106 having a front imaging lens 108. Immediately forward of the camera lens 108 is a spring loaded lens assembly 110 including a lens barrel 112 and lens 114. The lens assembly 110 is positioned within a fitted cylindrical cavity 116 and is biased towards the forward end of the cavity 116 by spring 118. At the top of the cavity 116 is a slot 120 for receiving a pin 122 downward into engagement in a circumferential groove 115 in the lens barrel 112. The slot and pin are so designed that the lens barrel can move longitudinally within the cavity 116 to achieve focusing of the camera on the viewing optics. The pin 122 is fastened to a follower nut 124 which rides on a lead screw 126. The lead screw 126 is driven by a coupler 128, which coupler is attached to a small gear motor 130. An opposite end of the lead screw is supported in a fixed brass bearing member 131. The end of the coupler 128 attached to the lead screw includes a bore in which a spring 132 is seated. An end of the lead screw 126 extends into the bore and is biased outwardly by the spring 132. The coupler includes a slot which engages a flange on the lead screw and allows the motor 130 to drive the lead screw through the coupler and cause the follower nut 124 to move longitudinally within the handle 100. The movement of the follower nut 124 correspondingly moves the lens assembly 110 allowing the user to focus an image appearing at the window end 134 of the handle onto the lens 108 of the camera 106.

One of the advantages of the present design is that the drive mechanism for the lens assembly 110 is capable of being over driven in either direction without becoming inoperative. The threaded portion of the lead screw 126 is less than the length of the follower nut 124 and may be, for example, about ⅛ inch in length. The threaded portion of the nut 124 is also short but selected to be at least as long as is needed to achieve focus for all uses of the endoscope. If the nut 124 is overdriven, the follower nut 124 can actually separate from the threaded portion of the lead screw 126, such as by the drive motor 130 being energized to rotate in one direction for an extended time. If the nut 124 is driven towards and into engagement with bearing member 131, lead screw 126 will be driven in an opposite direction such that coupler 128 further depresses spring 132. Spring 132 maintains a force on lead screw 126 so that the threads of the screw and those of nut 124 are urged towards one another. Consequently, when the motor 130 reverses direction, the threads engage and allow the nut to move on the lead screw. If the lead screw is driven in the reverse direction for an extended time, nut 124 will drive off the opposite end of the threaded portion of the lead screw 126. In that event, the spring 118 exerts a force through pin 122 via lens assembly 110 to urge nut 124 in an opposite direction so as to engage the threads of the nut and lead screw when the motor drive reverses.

In the embodiment of FIG. 8, the primary functions of imaging and lighting from the end of the endoscope are handled through the length of the handle 100 so that there are no protruding tubes or wires to interfere with the use of the endoscope. However, there is one additional probe input that protrudes through the probe end 102. Referring to FIG.

Figure 11A:
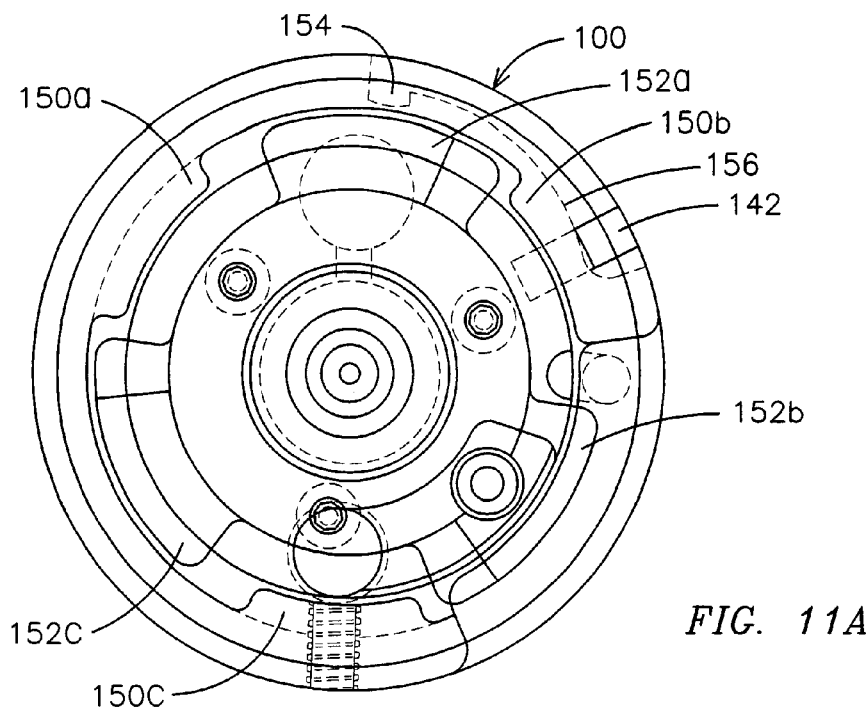
FIGS. 11a and 11b are end views of the handle of FIG. 9 showing the handle to probe coupling system.
Figure 11B:
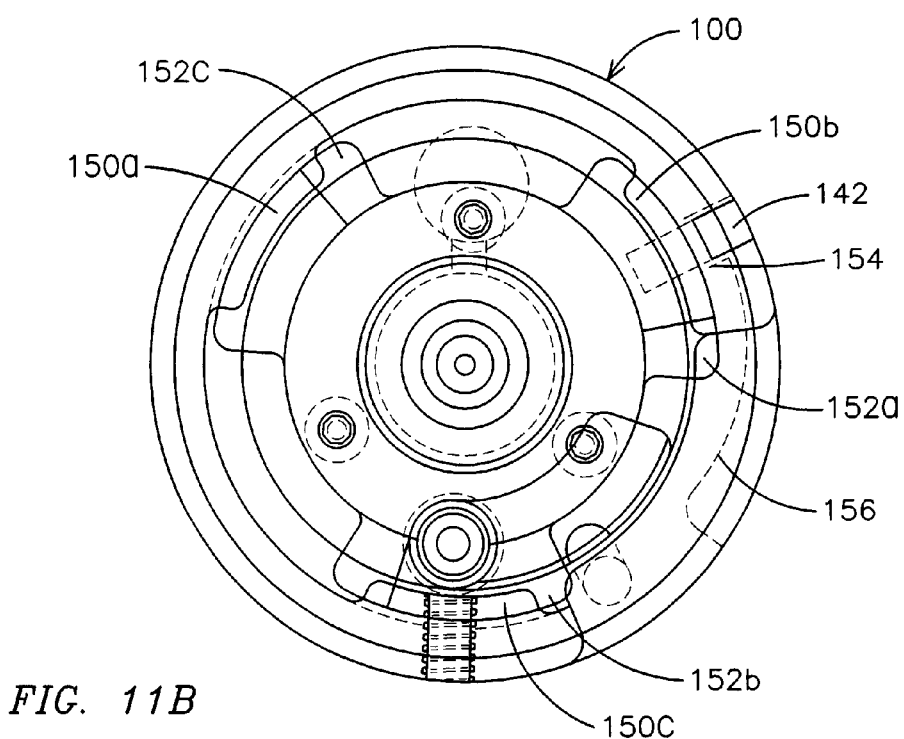

10, the end of the handle 100 is shown in engagement with the probe 102 with the handle rotated so as to illustrate positioning of one external guide rod 140 for passage of air or fluid for use in eye surgery. One of the advantages of the present invention is that the probe end 102 separates from the handle 100 by merely depressing a locking lever 142. When the lever 142 is depressed, the probe assembly can be rotated and separated from the handle assembly. The arrangement of the contacts within the probe assembly are such that positive locking is established between the probe assembly and handle. Referring to FIGS. 11a and 11b, there are shown end views of the handle with the mating elements of the probe in an insert position and in a locked position illustrating how the probe rotates using a bayonet type of connection to quickly attach or remove a particular probe and yet assure positive alignment between the probe and handle. The handle 100 has three cantilevered and tilted flanges 150a, 150b and 150c which extend radially inward. Probe portion 102 incorporates three mating flanges 152a, 152b and 152c. When probe portion 102 is pressed into engagement with handle 100, the flanges 152 fit into spaces intermediate flanges 150. Rotation of probe portion 102 allows flanges 152 to rotate under flanges 150. Since flanges 150 are tilted or angled circumferentially, such rotation tightens the engagement between probe portion and handle and pulls the two sections together. The locking lever 142 establishes the final engagement position by slipping into a slot 154 in probe portion 102. A cam surface 156 on probe portion 102 is used to raise the lever 142 as the probe portion is rotated. The slot 154 is located at the end of the cam surface 156. The locking lever 142 fits into the slot 154 in the probe when the probe is properly positioned with regard to the handle so as to accurately place the probe onto the handle. While the locking lever is illustrated as having a substantially rectangular cross section, it will be appreciated that the end which engages into the probe to assure proper positioning with respect to the handle could in fact be tapered to assure exact placement of the angular orientation of the probe 102 with respect to the handle 100.

The present invention also includes the method of use of an endoscope system. Such method includes the steps of providing the components as described above as well as the steps of illuminating and/or viewing and/or lasing and/or washing with such components and the further step of uncoupling and coupling the needle component and handle component and interchanging such components for a particular application.

What is claimed is:

1. An endoscope comprising:
   a handle;
   a probe extending from one end of the handle;
   a lens extending through the probe;
   a movable focusing lens positioned in the handle and aligned with the lens in the probe;
   an electric motor drive system mounted in the handle and coupled to the focusing lens for electrically driving the focusing lens longitudinally in the handle, the motor drive system including an electric motor; a lead screw; a nut follower threadedly mounted on the lead screw; a coupler for drivingly connecting the electric motor to the lead screw; and
   spring biasing means for urging the nut follower into engagement with threads on the lead screw when the nut follower is overdriven with respect to threads on the lead screw.

2. The endoscope of claim 1 and including a lens barrel for supporting the focusing lens, the lens barrel being restrained within a longitudinal guiding cavity within the handle.

3. The endoscope of claim 2 and including means coupling the nut follower to the lens barrel.

4. The endoscope of claim 3 wherein the spring biasing means includes a spring acting against the lens barrel.

5. The endoscope of claim 4 wherein the spring biasing means include a spring acting to urge the lead screw in a longitudinal direction in the handle.

6. The endoscope of claim 1 and including a bayonet type coupling for attaching the probe to the handle.

7. The endoscope of claim 6 and including a locking lever extending longitudinally along the handle and pivotable to engage a slot in the probe.

8. The endoscope of claim 7 and including a cam surface on the probe for raising the locking lever as the probe is rotated with respect to the handle, the slot in the probe being located at an end of the cam surface.

9. The endoscope of claim 8 wherein the bayonet type coupling comprises a plurality of cantilevered, radially inward extending flanges on the handle and a corresponding plurality of mating outwardly extending flanges on the probe, the probe flanges sliding under the handle flanges by rotating of the probe with respect to a longitudinal axis of the handle.

10. An endoscope comprising:
    a handle housing a means for viewing an image;
    a focusing lens disposed within a first cavity of the handle in optical communication with the means for viewing an image;
    means for longitudinally translating the focusing lens within the first cavity to adjust the focus of the endoscope including an electric motor; a lead screw rotationally disposed within the handle and having a threaded portion, the electric motor coupled to the lead screw for selectively rotating the lead screw; a follower nut disposed on the lead screw and having an interior threaded portion for engaging the threaded portion of the lead screw so that the follower nut may be longitudinally translated in response to rotation of the lead screw; and
    means for engaging the lead screw and the focusing lens in fixed relation so that the lens barrel is longitudinally translated in response to the longitudinal translation of the lead screw;
    a probe for holding a needle having an axially oriented major bore housing a first lens; and
    means for releasably coupling the handle and the probe so that the first lens housed within the axially oriented major bore is axially aligned with the focusing lens.

11. The endoscope of claim 10, the means for viewing an image comprising a camera having a front imaging lens in optical communication with the focusing lens.

12. The endoscope of claim 10, the means for longitudinally translating the focusing lens comprising:
    a power source;
    a coupler disposed within a second cavity of the handle and being operatively connected to the power source;
    a lead screw having a threaded portion, a first end and a second end, the first end rotatably engaged with the coupler;
    a fixed member disposed with the second cavity, the second end of the lead screw rotatably engaged with the fixed member;
    a follower nut disposed on the lead screw and having an interior threaded portion for engaging the threaded portion of the lead screw so that the follower may be longitudinally translated within the second cavity in response to rotation of the lead screw;

a lens barrel housing the focusing lens; and means for engaging the lead screw and the lens barrel in fixed relation so that the lens barrel is longitudinally translated in response to the longitudinal translation of the follower nut.

13. The endoscope of claim 12, the means for engaging the lead screw and the lens barrel in fixed relation comprising:

a circumferential groove formed within an exterior surface of the lens barrel; and a pin affixed to the lead screw that engages the circumferential groove.

14. The endoscope of claim 12 further comprising:

means for urging the follower nut and the lead screw into engagement when the interior threaded portion of the follower nut is overdriven with respect to the threaded portion of the lead screw.

15. The endoscope of claim 14, the means for urging the follower nut and the lead screw into engagement comprising:

a first biasing means for biasing the lead screw in a direction with respect to which the follower nut has been overdriven so that the interior threaded portion of the follower nut reengages the threaded portion of the lead screw.

16. The endoscope of claim 15, the means for urging the follower nut and the lead screw into engagement further comprising:

a second biasing means for biasing the lens barrel in a direction with respect to which the follower nut must be translated for the interior threaded portion of the follower nut to reengage the threaded portion of the lead screw; and means for reversing the rotational direction of the lead screw to cause the follower nut to translate in a direction opposite of that with respect to which the follower nut was overdriven.

17. The endoscope of claim 16, the second biasing means comprising a spring disposed within the first cavity.

18. The endoscope of claim 15, the first biasing means comprising a spring disposed within a bore formed in the coupler.

19. The endoscope of claim 10, the means for releasably coupling the handle and the probe comprising:

a first plurality of cantilevered and tilted flanges disposed on the handle that extend radially inwardly; and a second plurality of mating outwardly extending flanges disposed on the probe such that when the probe is pressed into engagement with the handle the second plurality of flanges fit into spaces between the first plurality of flanges whereby rotation of the probe allows the second plurality of flanges to rotate underneath the first plurality of flanges to pull the handle and probe together.

20. The endoscope of claim 19, the means for releasably coupling the handle and the probe further comprising:

a locking lever extending longitudinally along the handle and pivotable to engage a slot in the probe.

21. The endoscope of claim 19 further comprising:

a liquid and gas tight seal disposed between the handle and the probe when coupled together.

22. The endoscope of claim 19 further comprising:

a cam surface on the probe for raising the locking lever as the probe is rotated with respect to the handle and wherein the slot in the probe is located at an end of the cam surface.

23. The endoscope of claim 10 wherein the probe comprises at least one non-axial connector for receiving a corresponding non-axial component of the endoscope and wherein the means for releasably coupling the handle and the probe ensures alignment of the non-axial connector and the non-axial component when the handle and the probe are releasably coupled.

* * * * *